United States Patent [19]

Brois et al.

[11] Patent Number: 4,794,146

[45] Date of Patent: * Dec. 27, 1988

[54] OIL ADDITIVES CONTAINING A THIOCARBAMYL MOIETY

[75] Inventors: Stanley J. Brois, Westfield; Antonio Gutierrez, Mercerville, both of N.J.

[73] Assignee: Exxon Research & Engineering Co., Florham Park, N.J.

[ * ] Notice: The portion of the term of this patent subsequent to Jan. 5, 2005 has been disclaimed.

[21] Appl. No.: 89,449

[22] Filed: Aug. 20, 1987

Related U.S. Application Data

[63] Continuation of Ser. No. 908,786, Sep. 18, 1986, Pat. No. 4,717,754, which is a continuation of Ser. No. 776,019, Sep. 13, 1985, abandoned, which is a continuation of Ser. No. 320,574, Nov. 21, 1981, abandoned, which is a continuation of Ser. No. 109,778, Jan. 7, 1980, abandoned.

[51] Int. Cl.$^4$ .................................................. C08F 8/34
[52] U.S. Cl. ............................. 525/331.8; 525/332.8; 525/333.1; 525/333.9; 525/351; 525/352; 528/481; 528/503
[58] Field of Search ............... 525/331.8, 332.8, 333.1, 525/333.9; 528/481, 503

[56] References Cited

U.S. PATENT DOCUMENTS

| | | | |
|---|---|---|---|
| 2,168,674 | 8/1930 | Loane et al. | 87/9 |
| 2,169,700 | 8/1939 | Loane et al. | 87/9 |
| 2,218,918 | 10/1940 | Loane et al. | 252/47 |
| 2,619,464 | 11/1952 | Otto | 252/47 |
| 2,680,759 | 6/1954 | Otto | 260/454 |
| 2,689,255 | 9/1954 | Craig et al. | 260/454 |
| 2,954,393 | 9/1960 | Haimsohn et al. | 260/454 |
| 3,149,141 | 9/1964 | Venerable et al. | 260/454 |
| 3,318,936 | 5/1967 | Sakai et al. | 260/454 |
| 3,330,763 | 7/1967 | Damrath | 252/47.5 |
| 3,382,215 | 5/1968 | Baum | 525/351 X |
| 3,647,849 | 3/1972 | Venerable et al. | 260/454 |
| 3,749,747 | 7/1973 | Fancher | 260/454 |
| 3,867,360 | 2/1975 | Jones | 525/351 |

FOREIGN PATENT DOCUMENTS

514052  10/1939  United Kingdom .

OTHER PUBLICATIONS

R. G. R. Bacon, Chapter 27, "Thiocyanates, Thiocyanogen, and Related Compounds," *Organic Sulfur Compounds*, edited by N. Kharasch, vol. 1, Pergamon Press, 1961, N.Y., Symposium Publications Division, pp. 306-325.
R. G. Guy, "Thiocyanogen Halides," *Mechanisms of Reactions of Sulfur Compounds*, vol. 3, pp. 57-61 (1968).
A. B. Angus and R. G. R. Bacon, "Thiocyanogen Chloride, Part I", *J. Chem. Soc., pp. 774-778 (1958).*
E. Reid, "Organic Chemistry of Bivalent Sulfur", vol. VI, 1966, pp. 62-65 and 220-221.
R. G. Guy et al, "Pseudohalogen Chemistry", *J. Chem. Soc.*, 1973, pp. 281-284.

*Primary Examiner*—Joseph L. Schofer
*Assistant Examiner*—Bernard Lipman
*Attorney, Agent, or Firm*—F. T. Johmann; J. B. Murray, Jr.

[57] ABSTRACT

An oil-soluble additive for lubricating oil applications is provided by the formation of an adduct of thiocyanogen halide and polyalkene, removal of the hydrogen halide from said adduct and thermal rearrangement of the product to provide a polyalkenyl isothiocyanate which can be subsequently derivitized to provide a thiocarbamyl moiety containing product having excellent sludge dispersement properties.

23 Claims, No Drawings

OIL ADDITIVES CONTAINING A THIOCARBAMYL MOIETY

CROSS REFERENCE TO RELATED APPLICATIONS

This a continuation of application Ser. No. 908,786, filed Sept. 18, 1986, now U.S. Pat. No. 4,717,754, which in turn is a continuation of Ser. No. 776,019, filed Sept. 13, 1985, now abandoned, which is a continuation of Ser. No. 320,574, filed Nov. 21, 1981, now abandoned, which is a continuation of Ser. No. 109,778, filed Jan. 7, 1980, now abandoned.

BACKGROUND OF THE INVENTION

1. Field of the Invention

This invention relates to sulfur- and nitrogen-containing compositions and in a more particular sense it relates to those compounds having a thiocarbamyl moiety adapted for use as additives in hydrocarbon oils. This invention relates also to hydrocarbon oils, especially lubricating oil compositions containing said sulfur- and nitrogen-containing compositions.

2. General Background

The problem of deterioration of hydrocarbon oils has been the cause of principal concern in the formulation of hydrocarbon oil compositions such as fuels and lubricating compositions. Deterioration of hydrocarbon oils results in the formation of products which are corrosive to the metal surfaces with which the oils come into contact. It results also in the formation of products which have a tendency to agglomerate to form sludge and varnish-like deposits.

In recent years it has been a common practice to incorporate into hydrocarbon oils chemical additives which are capable of inhibiting the deterioration of oil and the formation of these harmful deposits. Such additives have generally been classified into three principal groups according to the manner in which they function to improve hydrocarbon oil. One group of such additives are the oxidation inhibitors which function to stabilize the oil against oxidative degradation. Another group of such additives are the corrosion inhibitors which counteract the corrosiveness of the products of oil degradation or passivate the metal surfaces against the corrosive action of such products. Still another group of such additives are the detergents or dispersing agents which function to maintain products of oil degradation in dispersion in the oil phase and to prevent the deposition of sludge and varnish.

Two or more such additives are often needed in a hydrocarbon oil to stabilize the oil against formation of harmful degradation products. The incorporation in an oil, however, of several different types of additives not only is costly, but is also dependent upon the compatibility of the additives with one another. Thus, it is known that additives which are effective separately may not be used in combination because of their incompatibility. A great deal of effort has recently been devoted to the development of so-called "multifunctional" additive, i.e., an additive which, by itself, is capable of imparting several desirable properties to an oil. It will be readily appreciated that the use of such additive is highly advantageous from the standpoint of both economy and convenience.

3. Prior Art Publications

Sulfur- and nitrogen-containing compositions are stated to provide such desirable multifunctional activity to both fuels and lubricating oils. For example, In U.S. Pat. No. 2,168,674 to Loane et al., mineral oils containing fatty acid thiocyanates, such as lauroyl thiocyanate and stearoyl thiocyanate, have been suggested as oxidation inhibitors for lubricating oils; in U.S. Pat. No. 2,169,700, the same inventors have disclosed mineral oils containing polythiocyanates having the formula, $R(SCN)_n$, wherein R is an aliphatic radical or an aromatic radical, and n is an integer greater than one; and, in U.S. Pat Nos. 2,619,464 and 2,680,759 it is reported that mineral lubricating oils containing small amounts of high molecular weight alkyl monothiocyanates, preferably $C_{21}$–$C_{34}$ monothiocyanates as paraffin wax monothiocyanates, are resistant to oxidation and have a reduced tendency to corrode hard metal alloy bearings (the polythiocyanates are noted as ineffective due to their substantial insolubility in mineral lubricating oils). The referenced latter compositions are produced by the reaction of an alkyl chloride with an inorganic salt of thiocyanic acid, e.g. ammonium thiocyanate, at a temperature of at least 100° C.

U.S. Pat. No. 3,330,763 discloses the use of hydrocarbylamine salts of thiocyanic acid as load-carrying additives in lubricating oils.

Further, the isomerization of allylic thiocyanates has been attributed to the occurrence of a cyclic intramolecular transition state (Organic Sulfur Compounds edited by N. Kharasch, Vol. 1, pg. 312, 1961, Pergamon Press, NY).

It is, accordingly, an object of this invention to provide novel compositions of matter.

It is also an object of this invention to provide compositions adapted for use as multifunctional additives in hydrocarbons, particularly for fuels and oils.

It is also an object of this invention to provide compositions useful as corrosion, oxidation inhibitors and/or dispersants in hydrocarbon lubricating oils.

SUMMARY OF THE INVENTION

In U.S. patent application Ser. No. 074,821 filed Sept. 12, 1979, now abandoned, of common assignee, it has been reported than an allylic thiocyanate resulting from the reaction of an alkenyl halide with potassium thiocyanate is, after isomerization to an isothiocyanate, susceptible to derivatization with protic reactants, particularly upon reaction with: amines, preferably alkylene polyamines: alcohols, preferably polyols; thiols; and, mixtures thereof to yield thiocarbamyl derivatives having activity in hydrocarbons, particularly fuels and lubricating oils.

It has now been discovered that a thiocyanogen halide, preferably ClSCN, can be readily added to a polyalkene to produce alkenyl isothiocyanates in high yield and purity. This had made possible the synthesis of: haloalkenyl isothiocyanates e.g. chloropolyisobutenyl isothiocyanate; alkenyl isothiocyano succinic anhydride, e.g. polyisobutenyl isothiocyano succinic anhydride; and poly(ethylene-$C_3$ to $C_8$ α-olefin-$C_4$ to $C_{30}$ diene) isothiocyanates and polyisothiocyanates.

The reaction of the invention comprises an equimolar reaction of a polyalkene e.g. an olefin such as polyisobutylene with a thiocyanogen halide e.g. thiocyanogen chloride to yield allylically unsaturated hydrocarbyl isothiocyanate which is susceptible to derivatization with protic reactants, particularly upon reaction with: amines, preferably alkylene polyamines: alcohols, preferably polyols; thiols; and, mixtures thereof to yield thiocarbamyl derivatives having activity in hydrocarbons, particularly fuels and lubricating oils.

It is a feature of this discovery that the presence of the isothiocyanate moiety provides the means for: reaction with compounds containing a labile hydrogen such as found in amines, alcohols, and thiols; reaction with substituted benzenes such as an alkyl substituted benzene; and, ring closure reactions such as with thioglycolic acids or esters.

DETAILED DESCRIPTION OF THE INVENTION

The present invention teaches the preparation of alkenyl isothiocyanates which involves a reaction of an alkene, preferably an olefin with at least an equal molar proportion of a thiocyanogen halide as illustrated by the following equation:

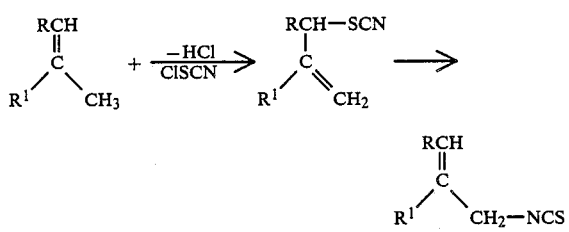

wherein R is polyalkyl and $R^1$ is hydrogen or alkyl.

Alkenes

The alkenes for the purpose of this invention are those unsaturated hydrocarbons which are capable of forming an olefin-Cl SCN adduct which eliminates HCl to form an allylic thiocyanate. The letter then undergoes rearrangement to the desired alkenyl isothiocyanate; unsaturated hydrocarbons include polypropylene, polyisobutylene, ethylene copolymers and terpolymers, polybutadiene and interpolymers of butylene and isoprene and preferably polyolefins and polymers possessing side chain unsaturation such as is exemplified by an ethylene-propylene-ethylidene norbornene terpolymer and poly(ethylene-propylene-hexadiene-1,4).

Thus, a variety of alkene and polyalkene types are suitable for reaction but certain types such as the di-, tri- and tetrasubstituted olefins are preferable since the adducts of more highly substituted alkenes are more susceptible to HCl elimination. Thus, oligomers of isobutylene, such as di-, tri- and tetraisobutylene, and polyisobutylenes with $(\overline{M}w)$ values ranging from about 300-100,000 are well suited as olefin substrates. Equally useful are substituted olefins, e.g. chloropolyisobutylene and polyisobutenyl succinic anhydride, ethylene-propylene terpolymers (especially that derived from ethylidene norbornene and LM butyl.) The present method does not appear to be limited by polyolefin mol. wt.

Thiocyanogen Halides

Thiocyanogen halides, including the iodide, bromide and chloride analogs are operative. Especially useful is ClSCN owing to its stability and ease of preparation from the chlorine, sulfuryl chloride or $S_xCl_2$ (x=1,2) by reaction with various thiocyanate salts such as NaSCN, KSCN, Pb (SCN)$_2$, and ammonium thiocyanate. In general, 0.2-0.5 molar solutions of thiocyanogen chloride in glacial acetic acid are prepared from KSCN and chlorine as described elsewhere (R. G. R. Bacon and R. G. Guy, J. Chem. Soc. 1960, p. 318, and 1961, p. 2428). Other suitable solvents include alcohols such as tetrahydrofuran (THF) and methanol. Usually the mixture is freed of metal halide salt by filtration and the supernatant containing the ClSCN reagent is added to the olefin reactant. However, in some instances one can simply add the olefin substrate directly to the mixture containing the ClSCN reagent, and the metal halide salt and subsequently remove the latter by filtration.

Reaction Conditions

Typically, the reaction of thiocyanogen chloride with diisobutylene and polyisobutylenes is exothermic and essentially complete within a few hours at room temperature. It is usually convenient to add the ClSCN reagent as an acetic acid, tetrahydrofuran, or alcohol solution to the olefin or poly (olefin) reactant; however, one can readily add the unsaturate to a solution of ClSCN and obtain high yields of the derived adduct. Ordinarily, a mole equivalent of ClSCN is used for each mole equivalent of unsaturation in the olefin reactant. Thus, equimolar amounts of a simple olefin and ClSCN are combined to give a 2-halo-thiocyanate intermediate which eliminates HCl and gradually rearranges to an unsaturated isothiocyanate product. Using more than one mole equivalent of ClSCN will afford a bis-adduct, which upon dehydrohalogenation and rearrangement yields the bis-isothiocyanate product.

In case of EP terpolymers and LM butyl, sufficient ClSCN is used to functionalize each site of unsaturation.

The in situ isomerization occurs after formation of the allylic thiocyanate in a manner which is believed to involve elimination of the halogen substituent, e.g. chloro, followed by rearrangement of the thiocyanate radical to generate the alkenyl isothiocyanate. The elimination of hydrogen chloride affords an allylic thiocyanate which rearranges to the corresponding alkenyl isothiocyanate as follows:

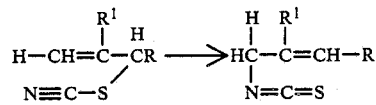

wherein $R^1$ and R is as earlier defined.

The resulting products thus include diisobutenyl isothiocyanate, octadecenyl isothiocyanate, polyisobutenyl ($C_{30}$-$C_{300}$) isothiocyanate, poly(ethylene-propylene-1,4-hexadiene) isothiocyanate, poly(ethylene-propylene-2,5-ethylidene-norbornene) isothiocyanate poly(ethylene-propylene) isothiocyanate and polyisobutenyl ($C_{30}$-$C_{300}$) isothiocyano succinic anhydride.

The isomerization can be facilitated by the presence of from 1 to 3% of a phase transfer agent to facilitate the elimination of the HCl which agents include quaternary ammonium compounds such as tetradodecyl ammonium chloride, cetyl trimethyl ammonium bromide and organic bases such as trialkylamines, e.g. tridecyl amine, tridodecyl amine, trihexylamine and tributylamine and other alkyl amines such as n-hexadecyl-amine, n-decylamine, dibutylamine and dipropylamine.

Reactions of the Alkenyl Isothiocyanates

As earlier discussed, the novel alkenyl isothiocyanates of the invention can be readily derivatized into thiocarbamyl compounds for enhanced additive activity by: reaction with compounds containing a labile hydrogen, preferably amines, alcohols and thiols; reaction with a benzene compound such as alkylated benzenes; and, ring closure with a thio compound such as thioglycolic acid.

A. The Amines

The reaction of the alkenyl isothiocyanate with an amine provides a thiourea derivative e.g. polyisobutenyl isothiocyanate reacted with diethylene triamine can be represented in part as follows:

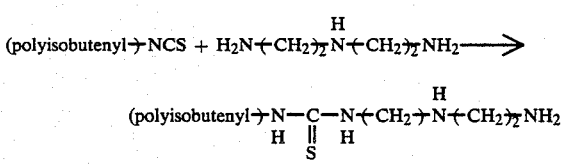

Useful amines are those compounds characterized by a radical having the structural configuration

and the two remaining valences of the nitrogen valences of the nitrogen atom of the

and above radical preferably are satisfied by hydrogen, amino, or organic radicals bonded to said nitrogen atom through direct carbon-to-nitrogen linkages. Thus, the compounds from which the nitrogen-containing group may be derived include aliphatic amines, aromatic amines, heterocyclic amines or carbocyclic amines. The amines may be primary or secondary amines and preferably are polyamines such as alkylene amines, arylene amines, cyclic polyamines, and the hydroxy-substituted derivatives of such polyamines.

Thus the useful amines include mono- and polyamines of 2 to 60, e.g. 3 to 20 total carbon atoms and from 1 to 12, e.g. 2 to 6 nitrogen atoms in the molecule. The amine compounds may be hydrocarbyl amines or may include hydroxy groups, alkoxy groups, amide groups or may be cyclic in structure such as imidazolines and the like.

The preferred amines are the alkylene polyamines having the following formulas:

(a) alkylene polyamines

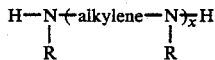

wherein x is an integer of 1 to 10, preferably 2 to 4, R is hydrogen, a hydrocarbon or substantially a hydrocarbon group containing 1 to 7, preferably 1 to 4 carbon atoms and the alkylene radical is a straight or branched chain alkylene radical having up to 7 preferably 2 to 4 carbon atoms;

(b) polyoxyalkylene polyamines

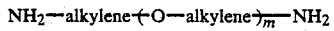     (i)

where m has a value of about 3 to 70 and preferably 10 to 35; and, $$R\text{-[alkylene-(O-alkylene)}_n\text{NH}_2]_{3-6} \quad \text{(ii)}$$

where n has a value of about 1 to 40 with the proviso that the sum of all the n's is from 3 to 70 and preferably from 6 to 35 and R is a polyvalent saturated hydrocarbon radical of up to 10 carbon atoms having a valance of 3 to 6. The alkylene groups in either formula (i) or (ii) may be straight or branched chains containing about 1 to 7 and preferably about 1 to 4 carbon atoms.

The alkylene polyamines of formula (a) above include, for example, methylene amines, ethylene amine, butylene amines, propylene amines, pentylene amines, hexylene amines, heptylene amines, octylene amines, other polymethylene amines, and the cyclic and higher homologs of these amines such as the piperazines, and the aminoalkyl-substituted piperazines. These amines include, for example, ethylene diamine, triethylene tetramine, propylene diamine, di(heptamethylene) triamine, tripropylene tetramine, tetraethylene pentamine, trimethylene diamine, pentaethylene hexamine di(trimethylene) triamine, 2-heptyl-3-(2-aminopropyl) imidazoline, 4-methylimidazoline, 1,3-bis-(2-aminoethyl) imidazoline, pyrimidine, 1-(2-aminopropyl) piperazine, 1,4-bis-(2-aminoethyl) piperazine, N,N-dimethylaminopropyl amine, N,N-dioctylethyl amine, N-octyl-N'-methylethylene diamine, and 2-methyl-1-(2-aminobutyl) piperazine. Other higher homologs which may be used can be obtained by condensing two or more of the above-mentioned alkylene amines in a known manner.

The ethylene amines which are particularly useful include diethylene triamine, tetraethylene pentamine, octaethylene nonamine, tetrapropylene pentamine, as well as various cyclic polyalkyleneamines. A particularly useful alkylene amine comprises a mixture of ethylene amines prepared by the reaction of ethylene chloride and ammonia which may be characterized as having a composition that corresponds to that of tetraethylene pentamine.

Alkylene amines having one or more hydroxyalkyl substituents on the nitrogen atoms may be used. These hydroxy-alkyl-substituted alkylene amines are preferably compounds wherein the alkyl group is a lower alkyl group, i.e. having less than about 6 carbon atoms and include, for example, N-(2-hydroxyethyl) ethylene diamine, N,N'-bis(2-hydroxyethyl) ethylene diamine, 1-(2-hydroxyethyl) piperazine, monohydroxypropyl-substituted diethylene triamine, 1,4-bis(2-hydroxypropyl)-piperazine, dihydroxypropyl-substituted tetraethylene pentamine, N-(3-hydroxypropyl) tetramethylene diamine, 2-heptadecyl-1-(2-hydroxyethyl) imidazole, etc.

The polyoxyalkylene polyamines of formula (b) above, e.g. polyoxyalkylene diamines and polyoxyalkylene triamines, may have average molecular weights ranging from about 200 to about 4000 and preferably from about 400 to 2000. The preferred polyoxyalkylene polyamines for purposes of this invention include the polyoxyethylene and polyoxypropylene diamines and the polyoxypropylene triamines having average molecular weights ranging from about 200 to 2000. The polyoxyalkylene polyamines are commercially available and may be obtained, for example, from the Jefferson Chemical Company, Inc. under the trade name "Jeffamines D-230, D-400, D-1000, D-2000, T-403", etc.

Other useful amine compounds include: alicyclic diamines such as 1,4-bis-(aminoethyl) cyclohexane, and heterocyclic nitrogen compounds such as imidazolines and N-aminoalkyl piperazines of the general formula:

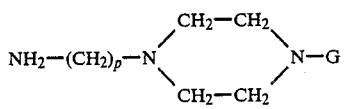

wherein G is independently selected from the group consisting of hydrogen, and ω aminoalkylene radicals of from 1 to 3 carbon atoms; and p is an integer of from 1 to 4. Nonlimiting examples of such amines include 2-pentadecyl imidazoline; N-(2-aminoethyl) piperazine; N-(3-aminopropyl) piperazine; and N,N'-di-(2-aminoethyl) piperazine.

B. The Alcohols a. Monohydric Alcohols

Useful monohydric alcohols can be characterized by the formula R'OH wherein R' is an alkyl or heteroalkyl group containing from 1 to 24, preferably 1 to 12, carbons such as methyl, ethyl, propyl, butyl, hexyl, octyl, decyl, lauryl, stearyl and mixtures thereof; and heteroatom-containing aliphatic radicals such as $CH_3O(CH_2CH_2O)_nCH_2CH_2-$, $CH_3S(CH_2CH_2S)_n-CH_2CH_2-$, $(CH_3)_2N(CH_2CH_2NCH_3)_nCH_2CH_2-$; etc. where n=1–10, and 1-aza-3,7-dioxabicyclo[3.3.0]oct-5-yl methanol. The resulting esters when used as additive components for mineral lubricating oils and fuels provide improved properties of antiwear, anticorrosion, friction modification or lubricity modification.

b. Polyhydric Alcohols

The polyhydric alcohols used in esterifying the isothiocyano compounds can have a total of 2 to 100 carbon atoms and can be represented by the formula:

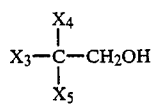

wherein: $X_3$ is hydrogen, $C_1$ to $C_5$ alkyl, hydroxyl, hydroxyalkyl $HO(CH_2)_n$ wherein n is 1–10, hydroxyalkoxy $HO(CH_2CH_2O)_n-$, wherein n is 1–40, hydroxyalkylthio $HOCH_2CH_2S(CH_2CH_2S)_n-$, wherein n is 1 to 10; and hydroxyalkylamino $HO(CH_2CH_2NCH_3)_n-$, wherein n is 1 to 10; and $X_4$ and $X_5$ may be the same or different and represent hydrogen, $C_1$ to $C_5$ alkyl and $C_1$ to $C_5$ hydroxyalkyl groups and their ester, ether, acetal, or ketal derivatives. Examples of useful acetals and ketals include mono- and bis-formals of pentaerythritol; mono- and bis-acetal and benzal analogs of pentaerythritol; and the cyclic formal and acetal of $HO(CH_2CH_2O)_nH$ wherein n is 4–8.

An especially preferred class of polyhydric alcohols are typified by pentaerythritol, dipentaerythritol, tripentaerythritol, polypentaerythritols, sorbitol, mannitol, cyclohexaamylose, cycloheptaamylose and related polyhydric alcohols such as these prepared via the aldol condensation of formaldehyde with ketones such as acetone, and cyclohexanone, e.g. 2,2,6,6-tetramethylol-1-cyclohexanol.

The esterification process is carried out according to conventional procedures by reacting from 0.25 to 1 moles of the alkenyl isothiocyanate to a mole of alkanol preferably the polyol at a temperature of from 50° C. to 200° C. until the reaction is complete by infrared monitoring of the reaction products until isothiocyanate absorption is absent.

c. The Thiols

In the preparation of the dithiocarbamic ester derivatives which conform to the formula

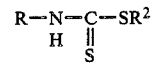

R is as earlier defined and $R^2$ represents a hydrocarbyl (both substituted and nonsubstituted) having from 2 to 100 carbons. Thus the hydrocarbon thiol reactant contains between 2 and 100 carbon atoms with an attached thiol or alkali or alkaline earth metal thiolate group. Suitable thiols include but are not limited to n-butyl mercaptan, isobutyl mercaptan, t-butyl mercaptan, hexyl mercaptans, octyl mercaptans, diisobutenyl mercaptan, decyl mercaptans, dodecyl mercaptans, cetyl mercaptans, cyclohexyl mercaptan, benzyl mercaptan, thiophenol and longer chain alkyl mercaptans derived from propene polymers and isobutylene polymers.

Other suitable reactants include monothio acids and dithio acids such as thioacetic, thiobenzoic, dithioacetic, dithiopropionic, and dithiobenzoic acid; useful thiophosphoric and esters include dialkyl dithiophosphoric and diaryl dithiophosphoric acid. The corresponding salts of the above acids, i.e. thioates, are equally useful.

Other thiol reactants are mercapto substituted azoles and azolines. Representative azoles include oxadiazoles, isoxazoles, isothiazoles, oxazoles, diazoles, triazoles, thiazoles, imidazoles, benzoxazole, benzimidazoles, etc. Representative azolines include thiazolines, oxazolines and imidazolines. Thus included are 2-mercapto-thiazole, 2-mercapto-oxazole, 2-mercapto-imidazole, 2-mercapto-thiazoline, 2-mercapto-oxazoline, 2-mercapto-imidazoline, 2-mercapto-benzothiazole, 2-mercapto-benzoxazole 2-mercapto-benzimidazole 2,5-dimercapto 1,3,4-thia-diazole and 3,5-dimercapto 1,2,4-thiadiazole.

USE OF THE ADDITIVE IN HYDROCARBON COMPOSITIONS

The isothiocyanate and thiocarbamyl reaction products of this invention can be incorporated into a wide variety of hydrocarbon compositions. They can be used in lubricating oil compositions, such as automotive crankcase lubricating oils, automatic transmission fluids, etc., in concentrations generally within the range of about 0.01 to 20 wt. %, e.g. 0.1 to 10 wt. %, preferably 0.3 to 3.0 wt. %, of the total composition. The lubricants to which the products of the invention can be added include not only hydrocarbon oils from petroleum, but also include synthetic lubricating oils such as polyethylene oils; alkyl esters of dicarboxylic acid; complex esters of dicarboxylic acid, polyglycol and alcohol; alkyl esters of carbonic or phosphoric acids; polysilicones; fluorohydrocarbon oils; mixtures of mineral lubricating oil and synthetic oils in any proportion, etc.

When the products of this invention are used in petroleum fuels such as gasoline, kerosene, diesel fuels, No. 2 fuel oil and other middle distillates to provide antirust properties, a concentration of the additive in the fuel of from 4 to 20 parts per million based on the weight of the total composition, will usually be employed.

The additives of the invention may be conveniently dispensed as an additive concentrate of from 2 wt. % to 100 wt. % with the balance conventionally a mineral lubricating oil e.g. up to 90 wt. %, with or without other additives being present.

In the above compositions or concentrates, other conventional additives may also be present including dyes, pour point depressants, antiwear agents such as $P_2S_5$-treated terpene or zinc dialkyl dithiophosphates of 3 to 8 carbon atoms in each alkyl group, antioxidants such as N-phenyl-α naphthylamine, ter-octylphenol sulfide, 4,4'-methylene bis (2,6-di-tert-butyl phenol), viscosity improvers such as ethylene-propylene copolymers, polymethacrylates, polyisobutylene, alkyl fumarate-vinyl acetate copolymers and the like, deemulsifiers such as polysiloxanes, ethoxylated polymers and the like.

The invention will be further understood by reference to the following examples, which include preferred embodiments of the invention.

EXAMPLE 1

Preparation of Thio-Cyanogen Chloride

Thio-cyanogen chloride can be prepared in a number of ways which are detailed hereafter.

A. An example of the preparation of thio-cyanogen chloride consists of dissolving 0.2 mole (ca. 19.4 g) of potassium thiocyanate in 200 ml of glacial acetic acid. The clear, colorless solution was stirred at 25° C. and 0.2 mole (ca. 15.0 g) of chlorine gas were bubbled into the solution for twenty-five minutes. The reaction mixture was kept at room temperature via external cooling. After the chlorine addition was completed, the reaction mixture was stirred for fifteen minutes and filtered. About 16 g of a white solid was collected, which upon infrared analyses showed it to be potassium chloride. The clear bright yellow solution of thio-cyanogen chloride in acetic acid can be used for subsequent reactions with olefins.

B. Another approach is to react potassium thiocyanate with sulfur dichloride in acetic acid or similar solvent solution reaction. Two-tenths mole (ca. 19.4 g) of potassium thio-cyanate were dissolved in 150 ml of acetic acid and stirred at room temperature. Thereafter, 0.2 mole (ca. 20.6 g) of sulfur dichloride were added dropwise for a period of 17 minutes. The addition of $SCl_2$ produced an exothermal reaction and a solid formed. The reaction temperature was kept about room temperature by the use of an external cooling bath. The resulting slurry can be used to react with an olefin. It is believed that the slurry contain a mixture of thio- and dithio-cyanogen chloride.

C. Another approach to producing the thio-cyanogen chloride is to react potassium thio-cyanate with sulfuryl chloride using a solvent medium such as tetrahydrofuran (THF). In this reaction, 0.2 mole (ca. 19.4 g) of potassium thiocyanate were slurried in 200 ml of THF and 0.2 mole (ca. 26.8 g) of $SO_2Cl_2$ were added dropwide for a period of twenty minutes. The addition produced an exothermic reaction causing the reaction temperature to climb to 42° C. at the end of the addition. A yellowish solid precipitated out of solution (potassium chloride). When the addition was completed, the reaction mixture was allowed to cool down to room temperature. The resulting slurry can be used to react, if desired, with an olefin. The solid was filtered and the THF solvent was evaporated producing 25 g of thio-cyanogen chloride.

D. In addition to thio-cyanogen chloride, it is believed possible to produce and use a dithio-cyanogen chloride. About 0.2 moles (ca. 19.4 g) of potassium thiocyanate were dissolved in 200 ml of acetic acid and 0.2 mole (27.0 g) of sulfur monochloride were added dropwise for a period of fifteen minutes. The addition caused an exothermic reaction and a solid precipitated out of solution. The reaction mixture was allowed to cool down to room temperature and stirred for a half hour. The resulting slurry can contain a mixture of mono-, di-, and tri-thiocyanogen chloride. The slurry can be used to react with olefins as desired.

EXAMPLE 2

Preparation of Diisobutenyl Isothiocyanate

Two-tenths mole (19.4 g) of KSCN were dissolved in 200 ml glacial acetic acid. The clear, colorless solution was stirred at 25° C. and 0.2 mole (17 g) of chlorine gas were bubbled into the solution which was kept at 25° C. by external cooling. After the $Cl_2$ addition, the reaction mixture was stirred at 25° C. for 15 minutes and then 0.2 mole (23 g) of diisobutylene (DIB-2) were added dropwise. The exothermic reaction was moderated by external cooling to maintain the reaction mixture at 25° C. After the DIB-2 addition, the mixture was stirred for an hour at 25° C. and filtered. The filter cake (KCl) weighed 16.1 g. The infrared spectrum of a concentrated sample of product featured bands at 4.6 (—SCN), 6.05 and 11.0 (C=C) microns and was consistent with a diisobutenyl thiocyanate structure [A]. Upon standing overnight, the latter rearranged in acetic acid almost exclusively to diisobutenyl-isothiocyanate [B]:

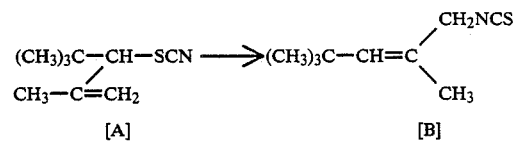

Vacuum distillation of the concentrated product (29.2 g) gave an amber liquid (b.p. 65° C. at 0.6 mm Hg) which featured an IR spectrum (strong, broad band at 4.6–4.8 microns), a UV spectrum (in cyclohexane) showing a λmax at 250 nm, and a proton NMR spectrum featuring signals centered at 5.45 (HC=C), 4.22 and 3.96 ($CH_2$—N), 1.8 ($CH_3$—O=) and 1.12

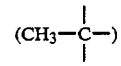

δ in the expected intensity ratio consistent with structure [B]. Prolonged heating at 150°–200° C. partially converted B into the isomeric isothiocyanate C.

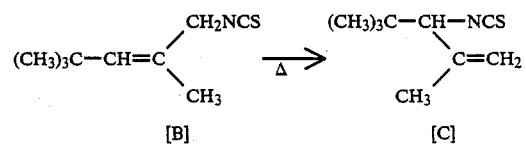

Later, it was found that substantial amounts of isomer C were formed directly from [A] in which the ClSCN addition to DIB-2 was effected in THF solution at room temperature (the ClSCN reagent was generated from either the chlorine or SCl₂ treatment of KSCN).

Elemental analyses were also consistent with the composition proposed for B: Analysis-calculated for $C_9H_{15}NS$: C, 63.84; H, 8.93; N, 8.28; S, 18.94. Found: C, 63.18; H, 8.91; N, 7.86; S, 19.39.

The infrared and proton spectra for C were also in full agreement with the proposed structure.

EXAMPLE 3

Preparation of Isomeric Diisobutenyl Isothiocyanates

KSCN (0.2 mole, 19.4 g) was slurried in 200 ml THF at room temperature, and converted into ClSCN via the addition of chlorine gas (0.2 mole, 15 g) at 25° C. (external cooling required). After addition, the reaction mixture was stirred at 25° C. and sparged with nitrogen. Thereafter, 0.2 mole (22.4 g) of diisobutylene-2 (DIB-2) were added dropwise as external cooling was needed to maintain the reaction temperature at 20° C. After DIB-2 addition, the mixture was stirred for a half-hour and filtered to remove the KCl salt. The concentrated mother liquor weighed 28 g (82% yield). The crude product analyzed for 62.54%C, 8.62%H, 8.15%N and 18.72%S. Gas chromatographic analysis at 170° C. on a 6'×¼" 20% Carbowax (20 m. on silica mesh supelcoport) column showed that the crude product was a 60/40 mixture of B and C, respectively. In contrast to reactions carried out in methanol and acetic acid which afforded mainly B, reaction in THF gives substantial yields of C. The ClSCN was generated via Cl₂ or SO₂Cl₂.

EXAMPLE 4

Preparation of Polyisobutenyl Isothiocyanate

About 1.0 mole (ca. 960 g) of a polyisobutylene having a number average molecular weight ($\overline{M}n$) of about 940 was dissolved in 500 ml of acetic acid and stirred at room temperature. Then, 200 ml of an acetic acid solution containing 1.0 mol of thio-cyanogen chloride were added for a period of fifteen minutes. The reaction temperature rose to about 30° C. by the end of the addition. Hydrogen chloride evolution was observed during this process. After the addition was completed, 200 ml of anhydrous ether were added to facilitate stirring, and the solution was stirred at room temperature for ten hours. The resulting solution was rotoevaporated at 80° C. under high vacuum until constant weight was obtained.

The infrared analysis of the residue showed to be the desired polyisobutenyl isothiocyanate. It analyzed for 2.46%S and 1.06%N. The sulfur-nitrogen ratio is 2.32; theory requires 2.28.

EXAMPLE 5

About 100 g (ca 0.1 mole) of a polyisobutylene of ($\overline{M}n$) of 940 were dissolved in 100 ml of acetic acid. To the above solution, 120 g of an acetic acid solution containing 0.2 mole of thiocyanogen chloride were added for a period of twenty minutes. An exothermic reaction and hydrogen chloride evolution were observed. The reaction mixture was diluted with 100 ml of chloroform and stirred at room temperature for about ten hours. The solvent was rotoevaporated at 80° C. under high vacuum until constant weight was obtained. The residue analyzed for 3.96%S and 1.71%N. The sulfur-nitrogen ratio is 2.31; theory requires 2.28.

EXAMPLE 6

Preparation of Isothiocyanate Poly(isobutylene-isoprene)

About 300 g of a toluene solution containing 0.0175 mole of a low molecular weight of a copolymer of isobutylene and 3 mole % isoprene having ($\overline{M}n$) of about 30,000 were stirred at room temperature while adding 0.05 mole of thio-cyanogen chloride in THF for twenty minutes. An exothermic reaction was observed during the addition. The reaction mixture was filtered and a clear bright yellow solution of poly(isobutylene-isoprene) isothiocyanate was obtained as analyzed by infrared spectroscopy.

EXAMPLE 7

Ethylene-Propylene Terpolymer Isothiocyanate

A freshly prepared thiocyanogen chloride solution in acetic acid was added dropwise to a toluene solution containing 0.017 mole of an ethylene propylene terpolymer (of 50 mole percent ethylene-4 wt. % of 5-ethylidene-2-norbornene and balance propylene and having a Mooney viscosity of 40 at 100° C.). An exothermic reaction took place and HCl evolution was observed during this addition. The solution was then stirred at room temperature overnight. The toluene and acetic acid were rotoevaporated at 100° C. until constant weight. The infrared analyses of the residue showed absorption bands ascribable to the desired copolymeric isothiocyanate.

EXAMPLE 8

In the same manner as in Example 7, 0.02 moles of thiocyanogen chloride in 100 ml of acetic acid were added to 0.017 moles of a terpolymer of 52 mole percent ethylene, 9 wt. % of 5-ethylidene-2-norbornene and balance propylene, said terpolymer having a Mooney viscosity of 50 at 130° C., in toluene. The reaction product was stirred at room temperature for ten hours and then rotoevaporated at 100° C. for six hours. The infrared analysis showed absorption bands characteristic of the desired poly(ethylene-propylene-5-ethylidene-2-norbornene) isothiocyanate product.

EXAMPLE 9

Reaction of Alkenyl Isothiocyanates with Amine Compounds

About 16.9 g (0.1 mole) of the diisobutenyl isothiocyanate (c) obtained in Example 2 were dissolved in 100 ml of THF and stirred at room temperature while 10.7 g (ca. 0.1 mole) of benzyl amine were added dropwise. Once the addition was completed, the reaction mixture was refluxed in THF for several hours until the infrared analysis showed complete disappearance of the isothiocyanate absorption band. The solvent was evaporated and the residue shown to be the desired thiourea as indicated by infrared. It satisfies the following structure

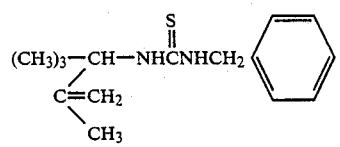

EXAMPLE 10

About 20 g of the product of Example 4 (ca. 0.02 mole) were diluted in 20 g of Solvent 150 mineral oil and stirred at room temperature while 2.8 g (ca. 0.02 moles) of N-aminopropyl morpholine were added. The reaction mixture was then heated to 150° C. and kept at this temperature for one hour. The oil solution was filtered while hot using a cellulite filter aid. The infrared analysis of the hazeless solution showed to be the desired thiourea. The oil solution analyzed for 1.16 wt. % nitrogen consistent with the desired product, i.e. N-poly(isobutenyl)-N'-3(1-morpholino) propyl thiourea.

EXAMPLE 11

About 10 g (ca. 0.01 mole) of the polyisobutenyl isothiocyanate of Example 4 was heated to about 80° C. and 1.9 g (ca. 0.01 mole) of tetraethylene pentamine were added. The reaction mixture was heated at 80° C. for one hour. The resulting product was diluted in Solvent 150 neutral to produce a 50% active ingredient material. The oil solution was filtered. The infrared analysis of the oil solution showed that the isothiocyanate band of 4.6–4.8 microns had disappeared. It contains absorption bands ascribable to the desired thiourea product. It analyzed for 3.2% nitrogen consistent with the desired product, i.e. N-poly(isobutenyl)-N'-(3,6,9,12-tetraaza dodecyl) thiourea.

EXAMPLE 12

Poly(isobutenyl) Isothiocyanate-Tris(hydroxymethyl) Aminomethane Adduct

About 10 g (ca. 0.01 mole) of the polyisobutenyl isothiocyanate of Example 4 was heated to about 80° C. and 1.21 g (ca. 0.01 mole) of tris(hydroxymethyl) aminomethane) were added. The reaction mixture was heated to 100° C. for one half hour. The product was diluted to produce a 50 wt. % active ingredient in Solvent 150 neutral. The filtered oil solution showed an infrared spectrum which indicated the disappearance of the 4.6–4.8 microns absorption band ascribable to the starting isothiocyanate.

EXAMPLE 13

About 10 g of the polyisobutenyl isothiocyanate of Example 4 was admixed with 2 g (ca. 0.01 mole) of cyclam, a cyclic amine called 1,4,8,11-tetraaza-cyclotetradecane and having a molecular weight of about 200 and having the following structural formula

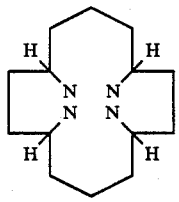

The reaction mixture was diluted in 100 ml of tetrahydrofuran and heated to reflux for ten hours. The THF solution was filtered and the solvent was evaporated. The oily residue was diluted to 50 wt. % active ingredient in Solvent 150 neutral. The infrared analysis of the oil solution showed the disappearance of the isothiocyanate absorption band at 4.8–4.9 microns.

EXAMPLE 14

About 20 g (ca. 0.02 mole) of the polyisobutenyl isothiocyanate of Example 4 was diluted in 20 g of Solvent 150 neutral mineral oil and heated to 150° C. Then, 2 g (ca. 0.01 mole) of a polyalkylene amine, DOW E-100, purchased from Dow Chemicals, Midland, Mich. were added while stirring at 150° C. The reaction product was nitrogen sparged at 150° C. for one hour and then filtered. The clear oil solution showed an infrared spectrum with no isothiocyanate absorption bands. The spectrum indicated that the desired thiourea product was obtained. It analyzed for 1.94 wt. % N.

EXAMPLE 15 1

The ethylene propylene terpolymer isothiocyanate product of Example 7 was dissolved in xylene and about 0.0175 moles of N-aminopropyl morpholine were added. The reaction mixture was heated to 100° C. for one hour with stirring. The infrared analysis of this product showed that the isothiocyanate band at 4.8–4.9 microns disappeared completely. The residue was diluted with Solvent 150 neutral mineral oil to 25% active ingredient and stripped under high vacuum at 100° C. until a constant weight was obtained.

The utility of the products made possible by the invention are shown by their use as dispersants in mineral oil lubricating formulations, e.g. the products of Examples 10 through 15, in at least a dispersing amount, preferably 0.5 to 10 wt. % and, as anti-oxidants in lubricating oils in at least an anti-oxidizing amount, preferably 0.01 to 1 wt. %.

The invention in its broader aspect is not limited to the specific details shown and described and departures may be made from such details without departing from the principles of the invention and without sacrificing its chief advantages.

What is claimed is:

1. A polyalkenyl isothiocyanate having the isothiocyanate group attached to a carbon which is one carbon removed from an ethylenically unsaturated carbon, said polyalkenyl isothiocyanate being obtained by the method of:
   (a) adding a solution of a thiocyanogen halide in acetic acid, tetrahydrofuran or alcohol solvent to a polyalkene to form an adduct wherein the polyalkene is selected from the group consisting of polypropylene, polyisobutylene, ethylene copolymers, ethylene terpolymers, polybutadiene-isoprene interpolymer, butylene-isoprene interpolymer, and mixtures thereof;
   (b) removing a hydrogen halide from said adduct to produce a polyalkenyl thiocyanate having the thiocyanate group attached is a carbon which is one carbon removed from an ethylenically unsaturated carbon; and
   (c) thermally rearranging said polyalkenyl thiocyanate to said polyalkenyl isothiocyanate.

2. A polyalkenyl isothiocyanate according to claim 1 wherein said polyalkene is a terpolymer of ethylene, propylene and a $C_4$ to $C_{30}$ diene.

3. A polyalkenyl isothiocyanate according to claim 1 wherein said polyalkene is polyisobutylene of $\overline{M}_w$ 300–100,000.

4. A polyalkenyl thiocyanate according to claim 1 wherein said polyalkene is an ethylene polymer of ethylene, propylene and 1,4-hexadiene.

5. A polyalkenyl isothiocyanate according to claim 1 wherein said polyalkene is a terpolymer of ethylene, propylene and 5-ethylidene-2-norbornene.

6. A polyalkenyl isothiocyanate according to claim 1 wherein said polyalkene is a copolymer of isobutylene and isoprene.

7. The polyalkenyl isothiocyanate according to claim 1 wherein the thiocyanogen halide is ClSCN.

8. The polyalkenyl isothiocyanate according to claim 7 wherein said polyisobutylene is of a $\overline{M}_w$ of 300-100,000.

9. The polyalkenyl isothiocyanate according to claim 1 wherein said steps (b) and (c) are effected in the presence of a phase transfer agent comprising a member selected from the group consisting of quaternary ammonium compounds and organic basis.

10. The polyalkenyl isothiocyanate according to claim 9 wherein said phase transfer agent comprises a member selected from the group consisting of tetradodecyl ammonium chloride, cetyl trimethyl ammonium bromide, tridecyl amine, tridodecyl amine, trihexylamine and tributylamine and other alkyl amines such as n-hexadecyl-amine, n-decylamine, dibutylamine and dipropylamine.

11. The polyalkenyl isothiocyanate according to claim 9 wherein said phase transfer agent is present in an amount of from about 1 to 3 percent.

12. A process for preparing a polyalkenyl isothiocyanate having the isothiocyanate group attached to a carbon which is one carbon removed from an ethylenically unsaturated carbon which comprises:
(a) adding a solution of a thiocyanogen halide in acetic acid, tetrahydrofuran or alcohol solvent to a polyalkene to form an adduct from the group consisting of polypropylene, polyisobutylene, ethylene copolymers, ethylene terpolymers, polybutadiene-isoprene interpolymer, butylene-isoprene interpolymer, and mixtures thereof;
(b) removing a hydrogen halide from said adduct to product a polyalkenyl thiocyanate; and
(c) thermally rearranging said polyalkenyl thiocyanate to said polyalkenyl isothiocyanate.

13. A process for preparing a polyalkenyl isothiocyanate according to claim 12 wherein said polyalkene is a terpolymer of ethylene, propylene, and a $C_4$ to $C_{30}$ diene.

14. A process for preparing a polyalkenyl isothiocyanate according to claim 12 wherein said polyalkene is polyisobutylene of $\overline{M}_w$ 300-100,000.

15. A process for preparing a polyalkenyl isothiocyanate according to claim 12 wherein said polyalkene is an ethylene polymer of ethylene, propylene and 1,4-hexadiene.

16. A process for preparing a polyalkenyl isothiocyanate according to claim 12 wherein said polyalkene is a terpolymer of ethylene, propylene and 5-ethylidene-2-norbornene.

17. A process for preparing a polyalkenyl isothiocyanate according to claim 12 wherein said polyalkene is a copolymer of isobutylene and isoprene.

18. A process for preparing a polyalkenyl isothiocyanate according to claim 12 wherein the thiocyanogen halide is ClSCN.

19. A process for preparing a polyalkenyl isothiocyanate according to claim 18 wherein said polyalkene is selected from the group consisting of polypropylene, polyisobutylene, ethylene copolymers, ethylene terpolymers, polybutadiene-isoprene interpolymer, butylene-isoprene interpolymer, and mixtures thereof wherein said polyalkene is polyisobutylene of 3-300 carbon atoms.

20. A process for preparing a polyalkenyl isothiocyanate according to claim 19 wherein said polyisobutylene is a $\overline{M}_w$ of 300-100,000.

21. A process for preparing a polyalkenyl isothiocyanate according to claim 12 wherein said polyisobutylene is a $\overline{M}_w$ of 300-100,000.

22. A process for preparing a polyalkenyl isothiocyanate according to claim 21 wherein said polyisobutylene is a $\overline{M}_w$ of 300-100,000.

23. A process for preparing a polyalkenyl isothiocyanate according to claim 21 wherein said polyisobutylene is a $\overline{M}_w$ of 300-100,000.

* * * * *